US010821290B2

(12) United States Patent
Villamil et al.

(10) Patent No.: US 10,821,290 B2
(45) Date of Patent: Nov. 3, 2020

(54) LEAD ADAPTOR DOUBLE PORT FOR IMPLANTABLE NEURO-STIMULATION SYSTEM

(71) Applicant: Greatbatch Ltd., Clarence, NY (US)

(72) Inventors: Luis Daniel Villamil, Montevideo (UY); Mathias de Souza, Montevideo (UY)

(73) Assignee: Greatbatch Ltd., Clarence, NY (US)

( * ) Notice: Subject to any disclaimer, the term of this patent is extended or adjusted under 35 U.S.C. 154(b) by 7 days.

(21) Appl. No.: 16/508,884

(22) Filed: Jul. 11, 2019

(65) Prior Publication Data
US 2020/0016414 A1 Jan. 16, 2020

Related U.S. Application Data

(60) Provisional application No. 62/697,568, filed on Jul. 13, 2018.

(51) Int. Cl.
*A61N 1/375* (2006.01)
*H01R 24/28* (2011.01)
(Continued)

(52) U.S. Cl.
CPC ......... *A61N 1/3752* (2013.01); *H01R 13/426* (2013.01); *H01R 13/5213* (2013.01);
(Continued)

(58) Field of Classification Search
CPC .... H01R 13/426; H01R 13/447; H01R 24/28; A61N 1/3752
(Continued)

(56) References Cited

U.S. PATENT DOCUMENTS

| 5,199,888 A * | 4/1993 | Condra | G06F 1/1616 |
| | | | 312/292 |
| 6,280,243 B1 * | 8/2001 | Liu | H01R 13/64 |
| | | | 439/502 |

(Continued)

*Primary Examiner* — Abdullah A Riyami
*Assistant Examiner* — Marcus E Harcum
(74) *Attorney, Agent, or Firm* — Michael F. Scalise (57) ABSTRACT

A cable assembly for a patient treatment system comprises an electrical cable having a proximal connector configured to connect to an external electrical stimulator device and a distal connector including a distal housing having an open distal end. The distal housing houses a manifold that supports a plurality of spring-loaded electrical contact assemblies aligned in two rows and being electrically connected to a corresponding one of a plurality of electrical contacts in the proximal connector. The housing distal open end is closed by a header that is movable between a closed position resting on the housing open end and an open position spaced there above. The header has a pair of side-by-side longitudinally extending openings. With the header in the open position, a practitioner holds the distal connector in one hand and with the other hand inserts the distal electrical contacts of one or two therapy delivery devices into the longitudinally extending openings. The practitioner then moves the header into the closed position to bring the distal electrical contacts of the therapy delivery devices into firm electrical contact with the spring-loaded electrical contact assemblies housed inside the distal housing.

23 Claims, 9 Drawing Sheets

US 10,821,290 B2
Page 2

(51) Int. Cl.
*H01R 13/52* (2006.01)
*H01R 13/426* (2006.01)
*H01R 107/00* (2006.01)

(52) U.S. Cl.
CPC ......... *H01R 24/28* (2013.01); *H01R 2107/00* (2013.01); *H01R 2201/12* (2013.01)

(58) Field of Classification Search
USPC .... 439/135, 136, 540.1, 638, 498, 502, 131, 439/909
See application file for complete search history.

(56) References Cited

U.S. PATENT DOCUMENTS

| | | | | |
|---|---|---|---|---|
| 6,466,718 | B1* | 10/2002 | Linnell | H01B 11/22 385/100 |
| 6,641,433 | B2* | 11/2003 | Devine | H01R 13/518 439/505 |
| 6,719,591 | B1* | 4/2004 | Chang | H01R 27/02 439/638 |
| 6,923,683 | B2* | 8/2005 | Dulai | H01R 27/02 439/638 |
| 6,991,483 | B1* | 1/2006 | Milan | H01R 27/00 439/171 |
| 7,086,898 | B2* | 8/2006 | Johnsen | H01R 24/547 439/579 |
| 7,128,614 | B1* | 10/2006 | Wu | H01R 13/6658 439/638 |
| 7,318,750 | B1* | 1/2008 | Chacon | H01R 27/02 200/51.03 |
| 8,133,072 | B2* | 3/2012 | Huang | H01R 12/778 439/502 |
| 8,888,500 | B2* | 11/2014 | Gao | H01R 13/17 439/39 |
| 8,996,128 | B2* | 3/2015 | Parker | A61N 1/0551 607/115 |
| 9,089,693 | B2* | 7/2015 | Swoyer | A61N 1/36053 |
| 10,653,000 | B2* | 5/2020 | Lo | H05K 1/0233 |
| 2006/0019542 | A1* | 1/2006 | Wu | H01R 25/00 439/638 |
| 2007/0212929 | A1* | 9/2007 | Huang | H01R 13/6658 439/498 |
| 2009/0099423 | A1* | 4/2009 | Al-Ali | H01R 13/6599 600/300 |
| 2011/0092081 | A1* | 4/2011 | Gao | H01R 9/03 439/40 |
| 2013/0017716 | A1* | 1/2013 | Elkhatib | H01R 13/6474 439/502 |
| 2013/0115821 | A1* | 5/2013 | Golko | H04L 12/40013 439/638 |
| 2013/0157500 | A1* | 6/2013 | Mattson | H04Q 1/135 439/502 |
| 2013/0309901 | A1* | 11/2013 | Hilbourne | G06F 1/1632 439/502 |
| 2014/0307809 | A1* | 10/2014 | Lo | H04B 3/50 375/257 |
| 2016/0118758 | A1* | 4/2016 | Cymerman | H01R 13/64 439/39 |
| 2019/0379150 | A1* | 12/2019 | Turksu | H01R 31/02 |

* cited by examiner

FIG. 14

LEAD ADAPTOR DOUBLE PORT FOR IMPLANTABLE NEURO-STIMULATION SYSTEM

CROSS-REFERENCE TO RELATED APPLICATION

This application claims priority to U.S. Provisional Application Ser. No. 62/697,568, filed on Jul. 13, 2018.

BACKGROUND OF THE INVENTION

1. Field of the Invention

The present invention describes a cable assembly for a patient treatment system. The cable assembly is configured to electrically couple a therapy delivery device, for example an implantable lead, to an external electrical stimulator device, for example a cardiac pacemaker or a cardiac defibrillator. The cable assembly of the present invention gives the practitioner the option of connecting one or two therapy delivery devices or leads to the external electrical stimulator device.

2. Prior Art

The prior art cable assembly for a patient treatment system described in U.S. Pat. No. 8,996,128 to Parker et al. includes an electrical cable having proximal and distal connectors. The proximal connector has a plurality of proximal electrical contacts that releasably connect to an exemplary external trial stimulator. The distal connector comprises first and second housing portions that are pivotably connected to each other for movement between a secured, closed position and an unsecured, open position. The first housing portion has an elongated slot that receives the proximal electrical contacts of a therapy delivery device or lead with the distal connector in the open position. The second housing portion has a plurality of distal electrical contacts that with the first and second housing portions secured together in the closed position electrically contact the signal delivery device positioned within the slot.

In use, a signal delivery device is first implanted in a patient. The proximal electrical contacts of the signal delivery device are then moved into the slot of the first housing portion of the distal connector, and the first and second housing portions are pivoted relative to each other to electrically connect the proximal electrical contacts of the signal delivery device to the distal electrical contacts carried by the second housing portion. The proximal connector of the cable assembly is then connected to an external trial stimulator to provide electrical stimulation to the patient through the implantable signal delivery device. The practitioner can then use the external trial stimulator to vary the stimulation parameters provided to the therapy delivery device in real-time to thereby select optimal or particularly efficacious parameters.

While the prior art cable assembly described by the '128 patent to Parker et al. works well for its intended purpose, pivoting the first and second housing portions between the closed and open positions can be cumbersome. Moreover, the first housing portion is only provided with one slot meaning the that the prior art cable assembly can only be connected to one implantable signal delivery device at a time. This limitation means that it can take more time for the practitioner to select optimal or particularly efficacious parameters for the external trial stimulator connected to two therapy delivery devices than when using the cable assembly of the present invention.

SUMMARY OF THE INVENTION

The present invention describes a cable assembly for a patient treatment system. The cable assembly is configured to electrically connect between an implantable signal delivery device, for example an implantable lead, to an external trial stimulator.

The cable assembly of the present invention is composed of an electrical cable having proximal and distal connectors. The proximal connector has a plurality of electrical contacts that are configured to connect to the external electrical stimulator device. The distal connector includes a distal housing having an open distal end. The distal housing houses a manifold that supports a plurality of electrical contact assemblies aligned in two rows, preferably of an equal number in each row. The electrical contacts assemblies are spring-loaded assemblies that are electrically connected to a corresponding one of the plurality of electrical contacts in the proximal connector via electrical conductors in the cable. The distal open end of the housing is closed by a header that is movable between a closed position resting or seated on the housing open end and an open position spaced above the housing open end. The header has a pair of side-by-side longitudinally extending openings that are aligned substantially perpendicular to an imaginary plane in which the distal ends of the plurality of electrical contact assemblies reside.

With the header in the open position, a practitioner holds the distal connector in one hand and with the other hand inserts the distal electrical contacts of one or two therapy delivery devices into the longitudinally extending openings. The practitioner then moves the header into the closed position, seated on the distal open end of the housing. This movement brings the distal electrical contacts of the therapy delivery devices into firm electrical contact with the spring-loaded electrical contact assemblies housing inside the distal housing. The spring-loaded feature for the electrical contact assemblies helps to augment and hold the electrical connections between the electrical contact assemblies of the cable assembly and the distal electrical contacts of the one or two therapy delivery devices.

The practitioner then uses the external trial stimulator connected to the proximal housing of the cable assembly of the present invention to vary the stimulation parameters provided to the therapy delivery devices in real-time. This helps the practitioner select optimal or particularly efficacious parameters including the positions of and the electrical signals provided by the therapy delivery devices. In a typical process, the practitioner uses the cable assembly of the present invention to temporarily connect the external trial stimulator to the signal delivery devices to test the efficacy of the therapy delivery devices in an initial position, then disconnect the cable assembly, reposition the therapy delivery device or devices, and reapply electrical stimulation. This process is performed iteratively until the practitioner obtains the desired position for the signal delivery devices.

These and other aspects of the present invention will become increasingly more apparent to those skilled in the art by reference to the following detailed description and to the appended drawings.

DETAILED DESCRIPTION OF THE PREFERRED EMBODIMENTS

The description that follows highlights spinal cord stimulation (SCS) systems, the treatment of pelvic floor disorders, and peripheral nerve field stimulation (PNFS). However, it is to be understood that the present invention relates to any type of implantable therapy delivery system with one or more therapy delivery devices comprising one or more electrodes or sensors. For example, the present invention may be used as part of a pacemaker, a defibrillator, a cochlear stimulator, a retinal stimulator, a stimulator configured to produce coordinated limb movement, a cortical stimulator, a deep brain stimulator, microstimulator, and in any other neural stimulator configured to treat sleep apnea, shoulder sublaxation, headache, and the like.

In another embodiment, one or more of the therapy delivery devices may be a fluid or drug delivery conduit, such as a catheter, including an inner lumen that is implanted to deliver a fluid, such as pharmaceutical agents, insulin, pain relieving agents, gene therapy agents, and the like from a fluid delivery system (e.g., a fluid reservoir and/or pump) to a respective target tissue site in a patient.

In yet another embodiment, one or more of the therapy delivery devices may be a medical electrical lead including one or more sensing electrodes to sense physiological parameters (e.g., blood pressure, temperature, cardiac activity, etc.) at a target tissue site within a patient.

In the various embodiments contemplated by the present invention, therapy may include stimulation therapy, sensing or monitoring of one or more physiological parameters, fluid delivery, and the like. The term "therapy delivery device" includes pacing or defibrillation leads, stimulation leads, sensing leads, fluid delivery conduits, and any combination thereof. The term "target tissue site" refers generally to the target site for implantation of a therapy delivery device, regardless of the type of therapy.

Figure 1:
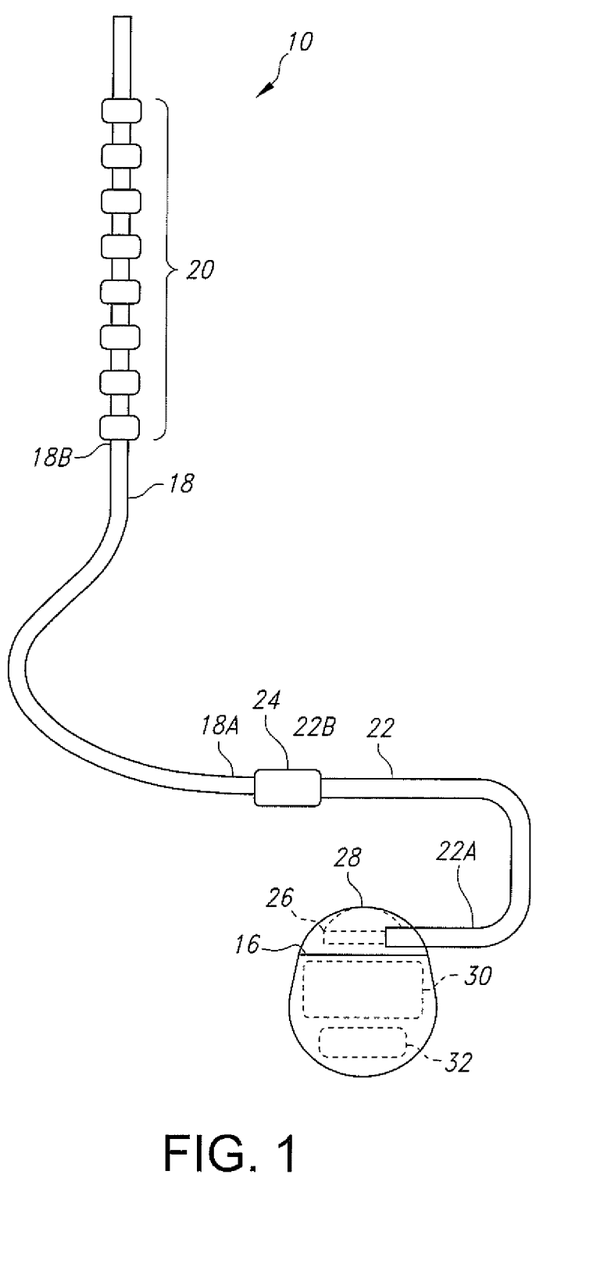
FIG. 1 is a schematic illustration of a therapy delivery system.
Figure 2:
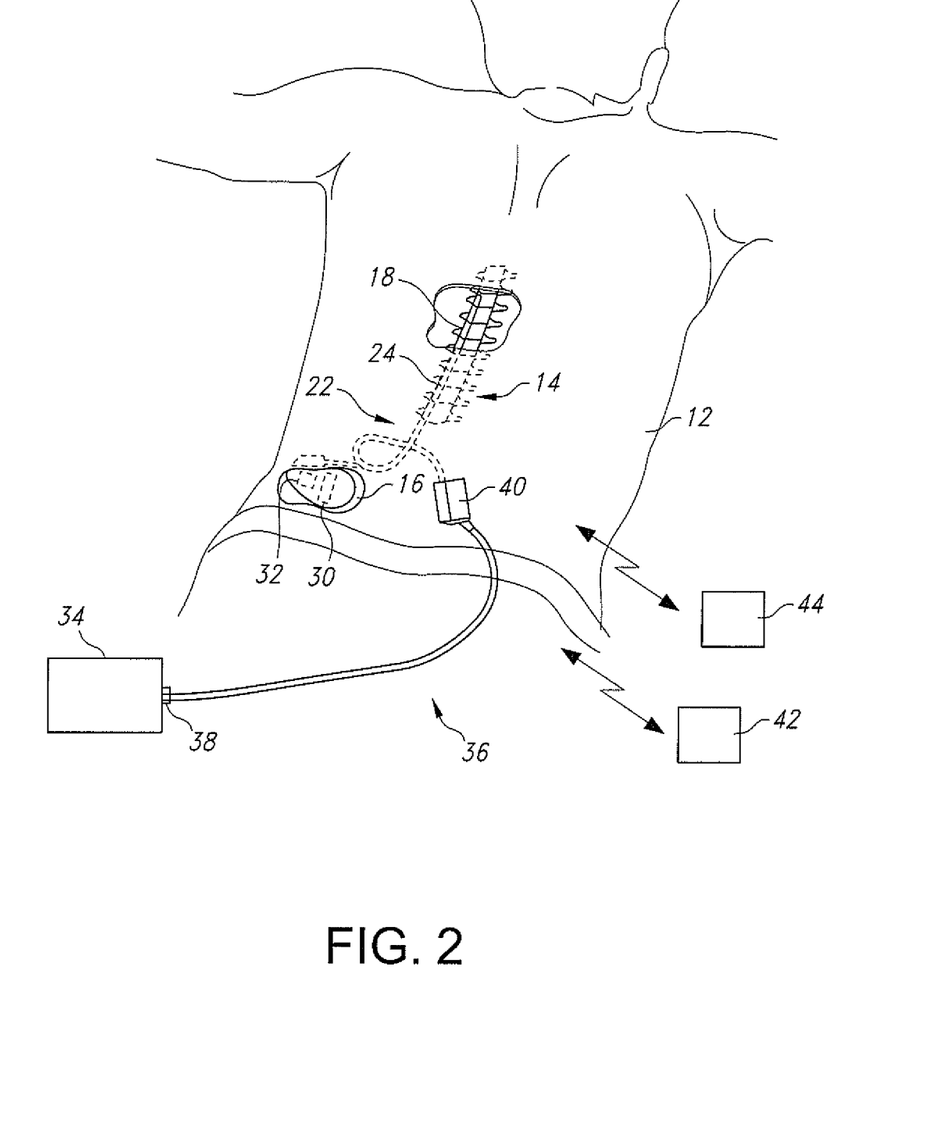
FIG. 2 is a partially schematic illustration of an implantable spinal cord stimulation system positioned at the spine to deliver a therapeutic signal in accordance with an embodiment of the present invention.

Turning now to the drawings, FIGS. 1 and 2 illustrate a generalized therapy delivery system 10 that may be used in stimulation applications, for example for electrical stimulation of a patient's 12 spinal cord 14 representing a target tissue site. The therapy delivery system 10 generally includes an implantable pulse generator 16 ("IPG"), an implantable therapy delivery device or lead 18, which carries an array of electrodes 20 (shown exaggerated for purposes of illustration), and an optional implantable extension lead 22. The electrodes 20 are typically rings or hollow cylinders that extend around a portion of the circumference of the therapy delivery device 18. Although only one therapy delivery device 18 is shown, typically two or more delivery devices are used with the therapy delivery system 10.

The therapy delivery device, for example lead 18 has a proximal end 18A and a distal end 18B. The lead 18 typically has a diameter ranging from about 0.03 inches to about 0.07 inches and a length ranging from about 30 cm to about 90 cm for spinal cord stimulation applications. The lead 18 may include a suitable electrically insulative coating, such as, a polymeric material (e.g., polyurethane or silicone).

In the illustrated embodiment, the proximal end 18A of the therapy delivery device 18 is electrically connected to the distal end 22B of the extension lead 22 via a connector 24. The proximal end 22A of the extension lead 22 is in turn electrically connected to the implantable pulse generator 16 via connector 26 associated with housing 28. Alternatively, the proximal end 18A of the therapy delivery device 18 is electrically connected directly to the connector 26.

In the illustrated embodiment, the implantable pulse generator 16 includes an electronic subassembly 30 (shown schematically), which includes control and pulse generation circuitry (not shown) for delivering electrical stimulation energy to the electrodes 20 of the therapy delivery device 18 in a controlled manner, and a power supply, such as a battery 32.

The implantable pulse generator 16 provides a programmable stimulation signal (e.g., in the form of electrical pulses or substantially continuous-time signals) that is delivered to a target stimulation site or sites by the electrodes 20. In applications with more than one therapy delivery device 18, the implantable pulse generator 16 may provide the same or a different signal to the electrodes 20.

The housing 28 is composed of a biocompatible material, such as for example titanium, and forms a hermetically sealed compartment containing the electronic subassembly 30 and battery 32 protected from the body tissue and fluids. The connector 26 is disposed in a portion of the housing 28 that is, at least initially, not sealed. The connector 26 carries a plurality of contacts that electrically couple with respective terminals at proximal ends of the therapy delivery device 18 or extension lead 22. Electrical conductors extend from the connector 26 and connect to the electronic subassembly 30.

Alternatively, the implantable pulse generator 16 can take the form of an implantable receiver-stimulator in which the power source for powering the implanted receiver, as well as control circuitry to command the receiver-stimulator, are contained in an external controller (not shown) inductively coupled to the receiver-stimulator via an electromagnetic link.

As shown in FIG. 2, in another embodiment, the implantable pulse generator 16 can take the form of an external trial stimulator (ETS) 34, which has similar pulse generation circuitry as an IPG 16 but differs in that it is a non-implantable device that is used on a trial basis after the therapy delivery device 18 has been implanted but prior to implantation of the IPG 16. The purpose of the ETS 34 is to test the responsiveness of stimulation that is to be provided by the therapy delivery device 18.

For example, a practitioner (e.g., a physician and/or a company representative) can use the external trial stimulator 34 to vary the stimulation parameters provided to the therapy delivery device 18 in real-time and select optimal or particularly efficacious parameters. These parameters can include the position of the therapy delivery device 18 as well as the characteristics of the electrical signals provided to the therapy delivery device.

In a typical process, the practitioner uses a cable assembly 36 according to the present invention to temporarily connect the external trial stimulator 34 to the signal delivery device 18. The cable assembly 36 accordingly includes a proximal connector 38 that is releasably connected to the external trial stimulator 34, and a distal connector 40 that is releasably connected to the therapy delivery device 18. The practitioner can test the efficacy of the therapy delivery device 18 in an initial position, then disconnect the cable assembly 36, reposition the therapy delivery device 18, and reapply electrical stimulation. This process is performed iteratively until the practitioner obtains the desired position for the signal delivery device 18. Optionally, the practitioner may move the partially implanted therapy delivery device 18 without disconnecting the cable assembly 36. In either embodiment, the practitioner will connect and disconnect the cable assembly 36 at least once during the process.

After the position of the therapy delivery device 18 and appropriate signal delivery parameters are established using the external trial stimulator 34, the patient 12 receives therapy via signals generated by the external trial stimulator 34, generally for a limited period. In a representative protocol, the patient 12 receives therapy for a one-week trial period. During this time, the patient wears the cable assembly 36 and the external trial stimulator 34 outside the body. Assuming the trial therapy is effective or shows the promise of being effective, the practitioner then replaces the external trial stimulator 34 and the cable assembly 36 with the implantable pulse generator 16 connected to the therapy delivery device 18 or connected to the lead extension 22 in turn connected to the therapy delivery device, and programs the pulse generator 16 with parameters selected based on the experience gained during the trial period. Optionally, the practitioner can also replace the therapy delivery device 18.

Once the implantable pulse generator 16 is positioned within the patient 12, the signal delivery parameters provided by the implantable pulse generator 16 can still be updated remotely via a wireless physician's programmer (e.g., a physician's remote) 42 and/or a wireless patient programmer 44 (e.g., a patient remote). Generally, the patient 12 has control over fewer parameters than does the practitioner. For example, the capability of the patient programmer 44 may be limited to starting and/or stopping the pulse generator 16, and/or adjusting stimulation amplitude.

Figure 3:
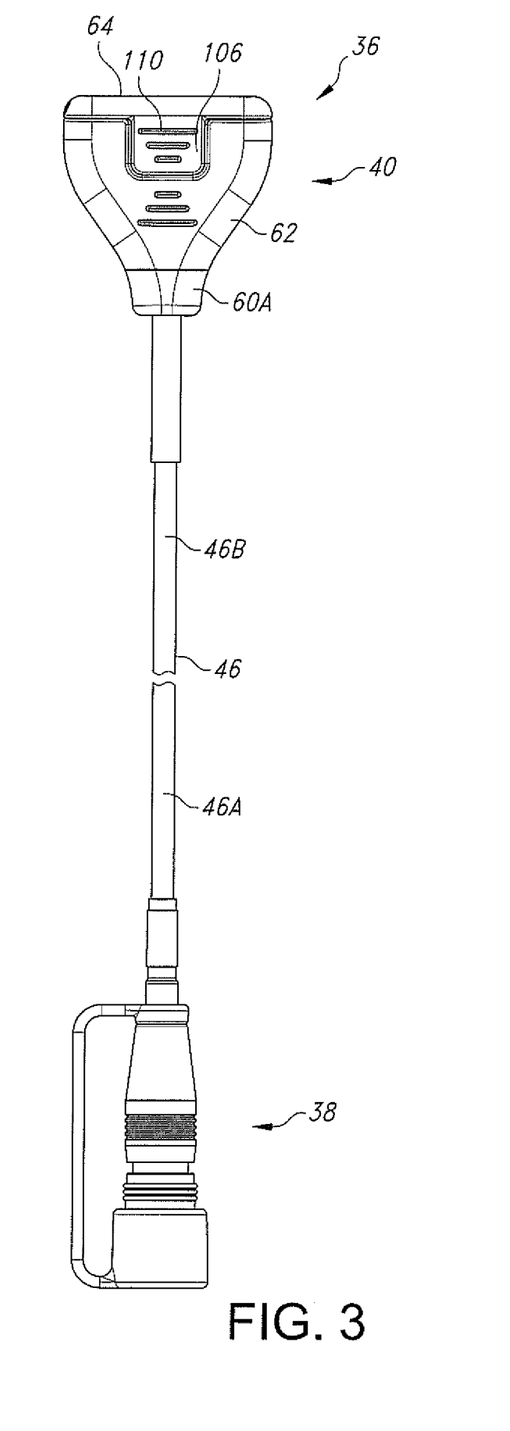
FIG. 3 is a front elevational view of a cable assembly 36 according to the present invention.

FIG. 3 illustrates a cable assembly 36 according to the present invention. The cable assembly 36 comprises a cable 46 formed from a plurality of electrical conductors 48 (FIGS. 7 to 9, 13 and 14) housed inside a polymeric sheath 50. The electrical conductors 48 extend from the proximal connector 38 connected to a proximal end 46A of the cable 46 to the distal connector 40 connected to a distal end 46B of the cable. The proximal and distal connectors 38, 40 each comprise a plurality of proximal and distal electrical contacts that are paired in electrical continuity with each other through one of the plurality of electrical conductors 48.

FIGS. 3 to 8 and 14 illustrate that when the proximal connector 38 is not connected to the external trial stimulator 34, its electrical contacts 50 are protected by an insulative cap 52 connected to the connector by a tether 54. The cap, which helps prevent fluid from contacting the electrical contacts 50, is easily removed from the proximal connector 38 to electrically connect the cable assembly 36 to the external trial stimulator 34. This electrical connection can be made by any one of many mechanisms with an exemplary threaded connection 56 being shown.

FIGS. 3, 4, 7 to 9 and 13 to 15 illustrate the distal connector 40 in greater detail including a distal housing 58 comprising a base plate 60 that is connected to a cover plate 62 to thereby form an open-ended body that is closed with a header 64. The base plate 60 has an annual collar portion 60A through which the distal end 46B of the cable 46 extends. A strain-relief sleeve 66 fitted onto the distal end 46B of the cable 46 is received in the collar 60A. The strain-relief sleeve 66 adds support to the cable 46 and helps prevent wear of the polymeric sheath 50 covering the plurality of electrical conductors 48.

Figure 13:
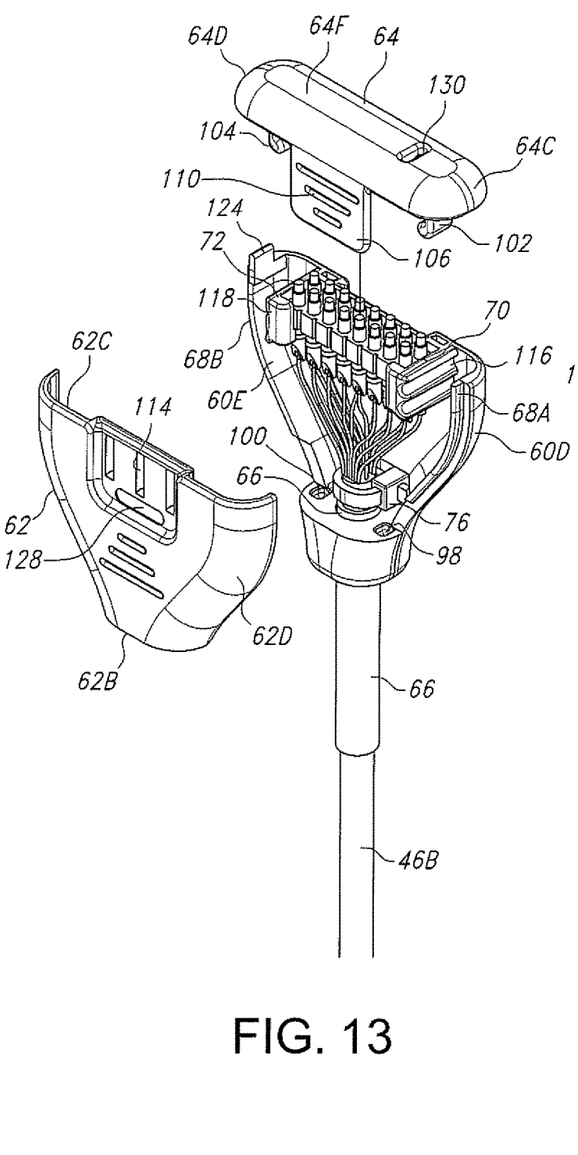
FIG. 13 is a perspective view of the distal connector 40 for the cable assembly 36 with the cover plate 62 and header 64 separated from the base plate 60.
Figure 14:
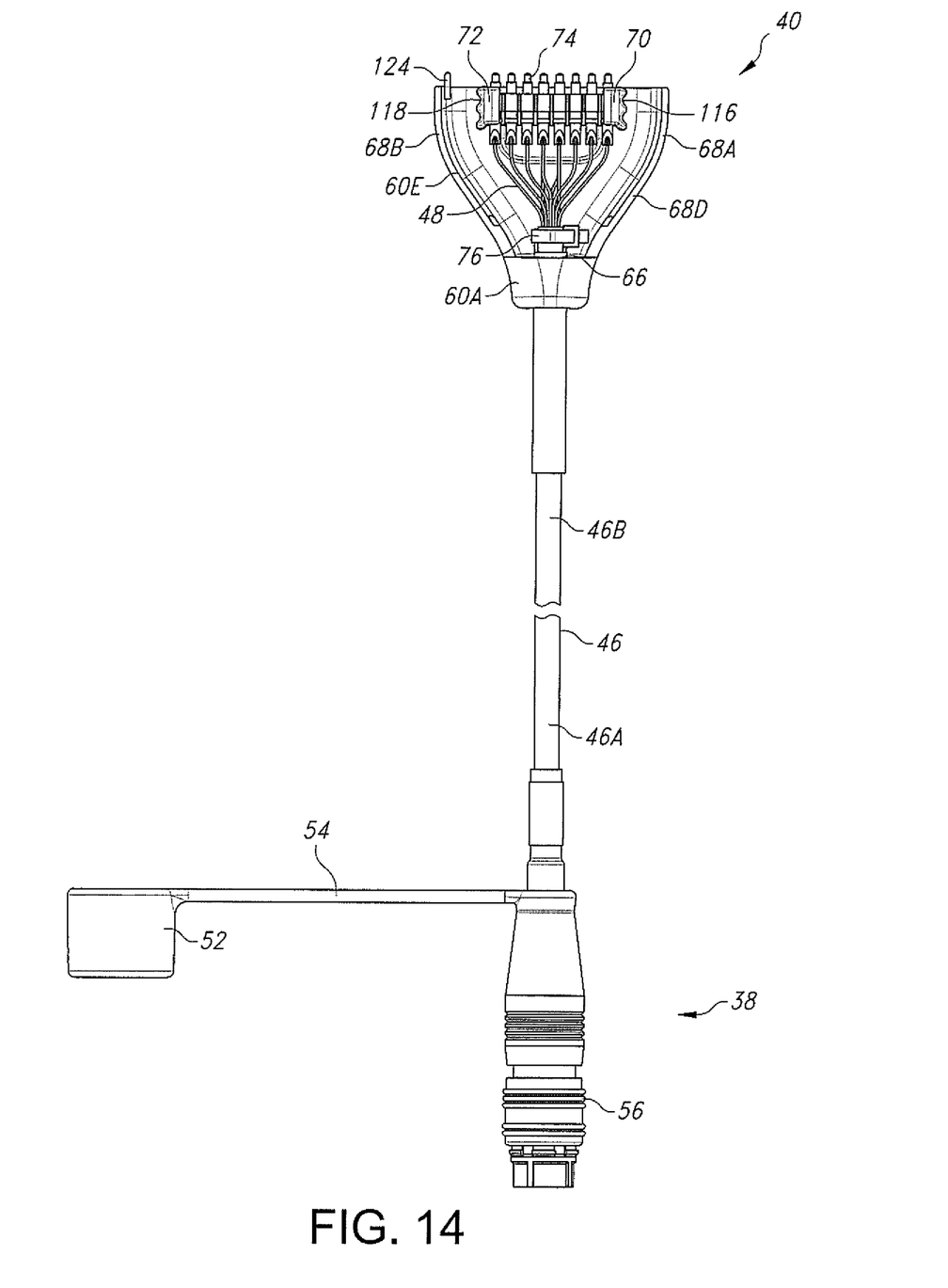
FIG. 14 is a front elevational view the distal connector 40 shown in FIG. 13 but without the cover plate 62 and header 64.

The base plate 60 comprises a main face wall 60B that widens or fans outwardly from the proximal collar 60A to a distal open end 60C. Opposed sidewalls 60D and 60E extend upwardly from the face wall 60B. The opposed sidewalls 60D, 60E each have an inner outwardly extending lip 68A and 68B, the significance of which will be described in detail hereinafter. A pair of inverted L-shaped connection tabs 70 and 72 extend upwardly from an inner surface of the face wall 60B. The connection tabs 70, 72 are spaced inwardly from the opposed sidewalls 600 and 60E, and each has an inwardly projecting protrusion 70A, 72A.

Figures 8, 9:
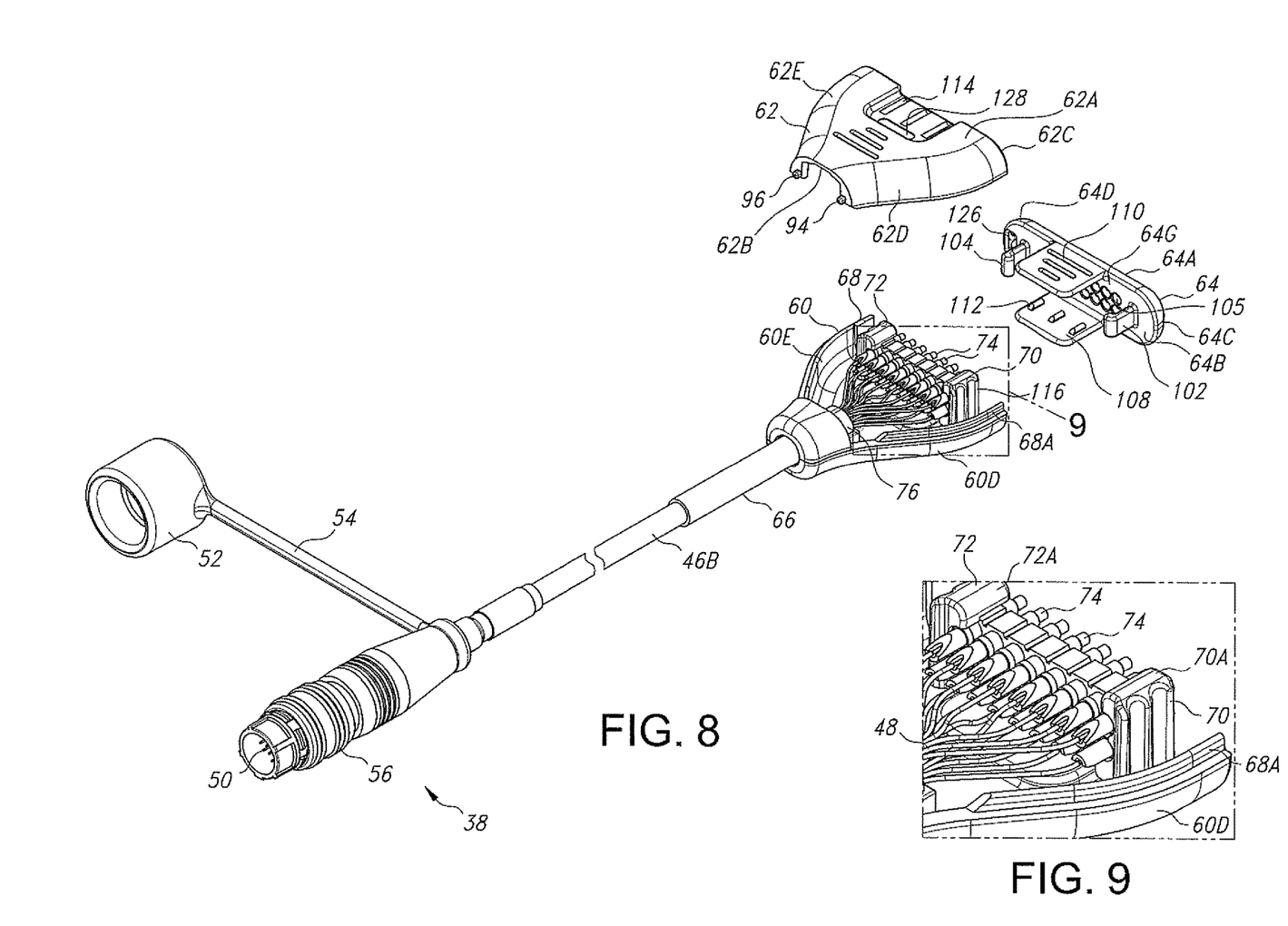
FIG. 8 is a perspective illustration of the cable assembly 36 with its distal connector 40 in an exploded view.
FIG. 9 is an enlarged view of the area indicated in FIG. 8.

As shown in FIGS. 8 and 13, the cover plate 62 comprises a main sidewall 62A that widens or fans outwardly from a proximal open end 62B to a distal open end 62C. Opposed sidewalls 620 and 62E extend upwardly from the main sidewall 60B.

FIGS. 8, 13 and 14 also show that the strain-relief sleeve 66 covering the polymeric sheath 50 at the distal end 46B of the cable 46 terminates inside the base plate 60, proximate the collar 60A. However, the electrical conductors 48 extend further outwardly into the base plate 60 where they are electrically connected to respective electrical contact assembly 74. A cable tie 76 (FIGS. 7 to 9, 13 and 14) secures the strain-relief sleeve 66 to the distal end 46B of the cable 46 inside the distal housing 58.

FIGS. 8, 9, 13 and 14 illustrate that there are an equal number of electrical contact assemblies 74 as there are electrical conductors 48. In the illustrative embodiment there are sixteen electrical contact assemblies 74 electrically connected to respective electrical conductors 48. However, it is within the scope of the present invention that there can be a greater or lesser number of electrical contact assemblies 74 and corresponding electrical conductors 48. The number of electrical contact assemblies 74 and corresponding electrical conductors 48 is only limited by the specific implantable therapy delivery system 10 that the cable assembly 36 is designed as a compatible accessory.

Figure 10:
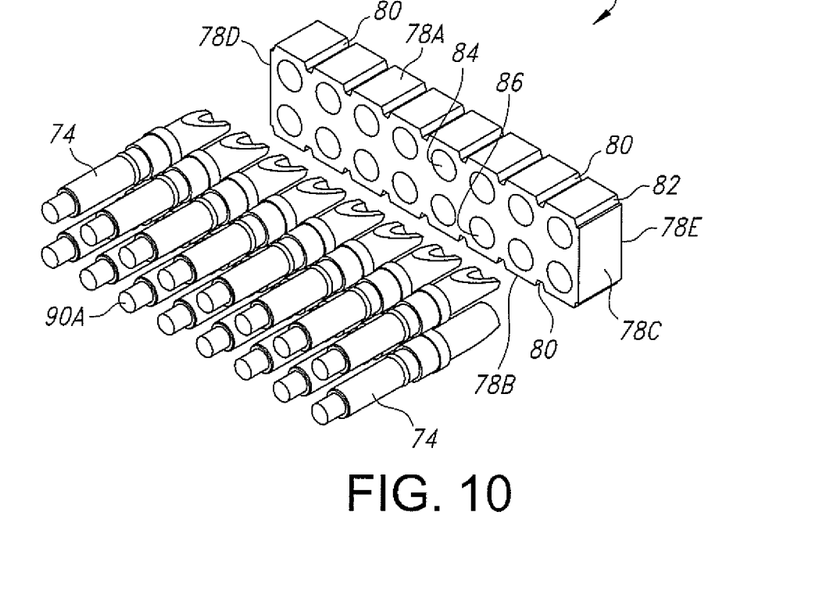
FIG. 10 is a perspective view showing sixteen electrical contact assemblies 74 prior to being supported in a manifold 78 of the distal connector 40.
Figure 11:
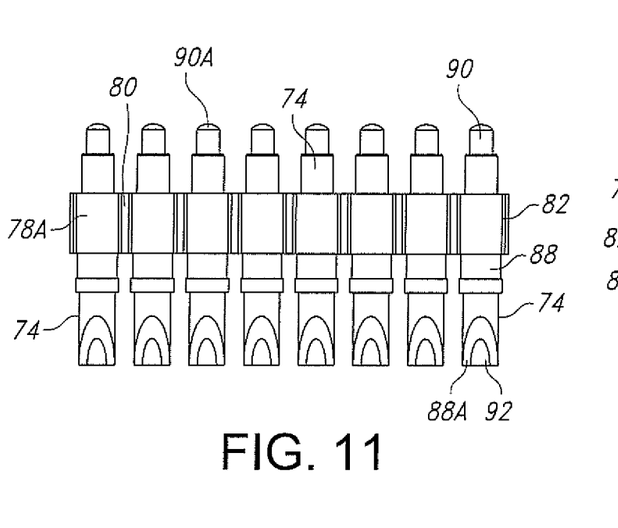
FIG. 11 is a front elevational view of the electrical contact assemblies 74 supported in the manifold 78 of the distal connector 40.
Figure 12:
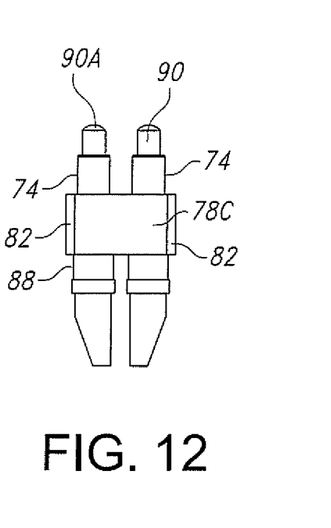
FIG. 12 is a side elevational view of the assembly shown in FIG. 11.

FIGS. 10 to 12 show that the sixteen electrical contact assemblies 74 are individually supported in a manifold 78. The manifold 78 is a plate-shaped member of an electrically insulative material, for example Nylon, having a thickness defined by a surrounding or annular sidewall comprising first and second sidewall portions 78A, 78B, both extending to opposed third and fourth end wall portions 78C, 78D, the sidewall wall and end wall portions extending to opposed proximal and distal face walls 78E and 78F.

A series of spaced-apart grooves 80 extend inwardly into each of the first and second sidewall portions 78A, 78B and meet the opposed proximal and distal face walls 78E, 78F. The grooves 80 in the first sidewall portion 78A are aligned across from those 80 in the second sidewall portion 78B. Moreover, there are partial grooves 82 at the corners where the first and second sidewall portions 78A, 78B meet the opposed third and fourth end wall portions 78C, 78D.

Two rows of via holes 84 and 86 extend through the thickness of the manifold 78. In the illustrated embodiment, there are two rows of eight via holes 84, 86 with pairs of via holes being aligned across from each other.

FIGS. 10 to 12 show that the sixteen via holes 84, 86 in the manifold 78 are sized to receive a respective one of the sixteen electrical contact assemblies 74. Each electrical contact assembly 74 is a rod- or cylindrically-shaped structure comprising a contact sleeve 88 supporting a distal contact pin 90 in a spring-loaded relationship. The distal contact pin 90 has a partial hemispherical or dome-shaped end 90A. As will be described in detail hereinafter, the spring-loaded relationship of the distal contact pin 90 with the contact sleeve 88 enables the contact pin to actuate axially back and forth along the contact sleeve 88 without the two cylindrically-shaped members separating from each other.

The contact sleeve 88 has a beveled proximal end 88A surrounding a bore hole 92 into which the bare end of one of the electrical conductors 48 is received. The beveled end 88A provides an operator or robotic-controlled machine with a clear line-of-sight for making a secure electrical connection of the electrical conductor 48 to the electrical contact sleeve 88. Solder or a laser weld is preferred for making these electrical connections.

With the sixteen electrical contact assemblies 74 electrically connected to a respective one of the sixteen electrical conductors 48, the dome-shaped distal end 90A of each of the distal contact pins 90 reside substantially along an imaginary plane. The cable 46 is then moved proximally until the manifold 78 is seated between the upwardly extending connection tabs 70, 72. In this position, the grooves 80 and partial grooves 82 of the manifold 78 are received in matching ridges 83 (FIG. 7) formed on the inner surface of the face wall 60B between the connection tabs 70, 72 and their respective inwardly projecting protrusions 70A, 72A.

As shown in FIG. 8, the cover plate 62, which is sized and shaped to mate with the base plate, has a pair of protrusions 94, 96 at its proximal open end 62B. These protrusions 94, 96 are received in matching openings 98, 100 in the annular collar 60A (FIG. 13) of the base plate 60 as the opposed sidewalls 60D, 60E are snap-fit into engagement with the outwardly extending lips 68A, 68B of the base plate 60.

As shown in FIGS. 3, 4, 8, 13 and 15, the distal housing 58 is closed with the header 64. The header 64 is a generally oval-shaped plate comprising opposed long and generally straight sidewalls 64A, 64B meeting opposed curved end walls 64C, 64D. The sidewalls 64A, 64B and the end walls 64C, 64D meet an upper surface 64F (FIG. 13) spaced from an inner surface 64G (FIG. 8) by a header thickness.

Inwardly facing L-shaped hooks 102, 104 depend from the inner surface 64G of the oval-shaped plate proximate the curved end walls 64C, 64D. The inner surface 64G of the header is provided with a plurality of recesses or inlets 105 (FIG. 8) into which the distal ends of the electrical contact assemblies 74 nest with the header 64 in the closed position shown in FIGS. 3, 4 and 15, but without the header having received a therapy delivery device 18 as will be described in detail hereinafter.

There is also a pair of finger tabs 106, 108 that depend from the plate centered about mid-way along the length of the straight sidewalls 64A, 64B. The finger tabs 106, 108 are provided with a number (for example three) of outwardly facing horizontal grooves 110 that enhance tactile feel and manipulation of the header 64. Further, the finger tabs 106, 108 are provided with a number (for example three) of inwardly facing vertical ridges 112 that mate with corresponding outwardly facing vertical grooves 114 in the base plate 60 and the cover plate 62. With the vertical ridges 112 having been moved proximally along the length of the vertical grooves 114, the L-shaped hooks 102, 104 snap-fit into engagement with at least two matching horizontal grooves 116, 118 on the respective connection tabs 70, 72. That is, the at least two horizontal grooves 116, 118 of the first pair of inwardly facing L-shaped hooks 70, 72 are in a snap-fit engagement with a second pair of inwardly facing L-shaped hooks 102, 104 of the header 64 to thereby define the closed position for the distal connector 40 with the second pair of L-shaped hooks 102, 104 of the header 64 in a snap-fit engagement with a proximal most one of the at least two horizontal grooves and to define the open position for the distal connector 40 with the second pair of L-shaped hooks 102, 104 of the header 64 in a snap-fit engagement with a distal most one of the at least two horizontal grooves 116, 118.

Figure 4:
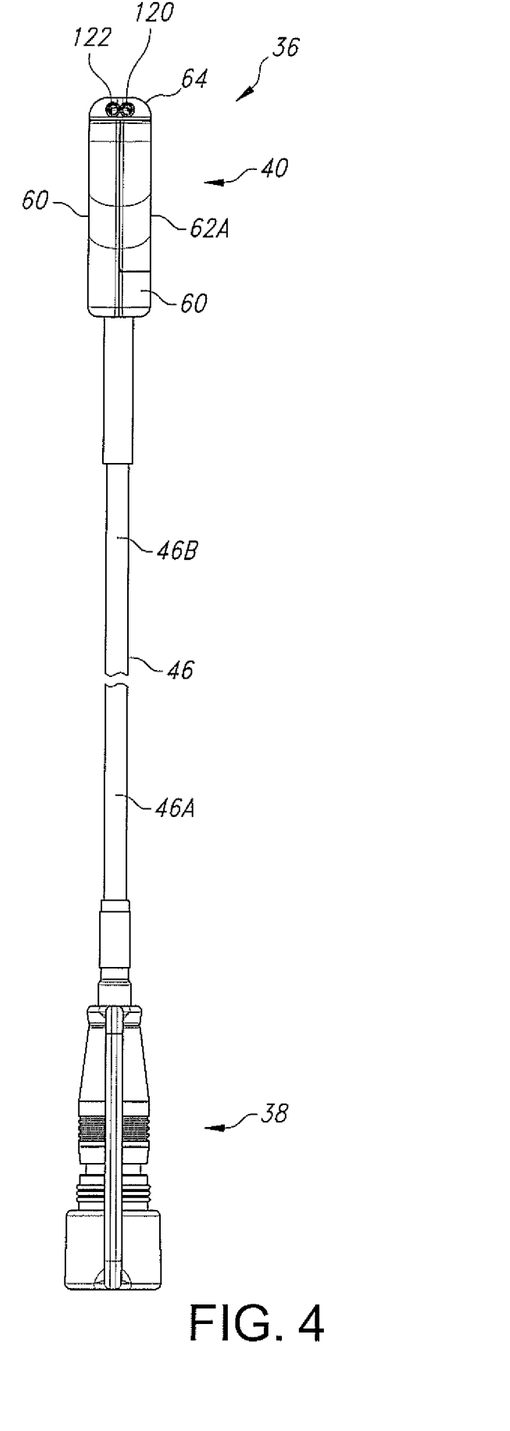
FIG. 4 is a side elevational view of the cable assembly 36 shown in FIG. 3.
Figures 5, 6:
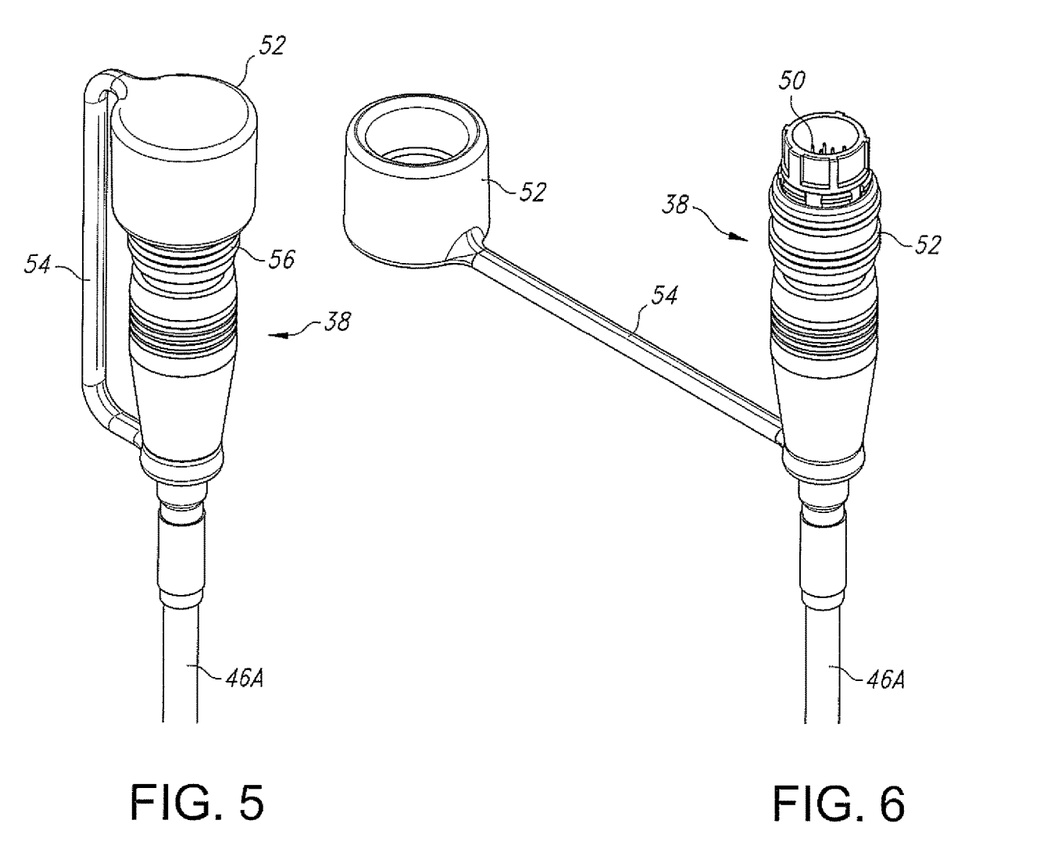
FIG. 5 is a perspective view of the proximal connector 38 for the cable assembly 36 shown in FIGS. 3 and 4.
FIG. 6 is a perspective view showing the proximal connector 38 with the protective cap 52 of FIG. 5 having been removed to expose electrical contacts 50.
Figure 7:
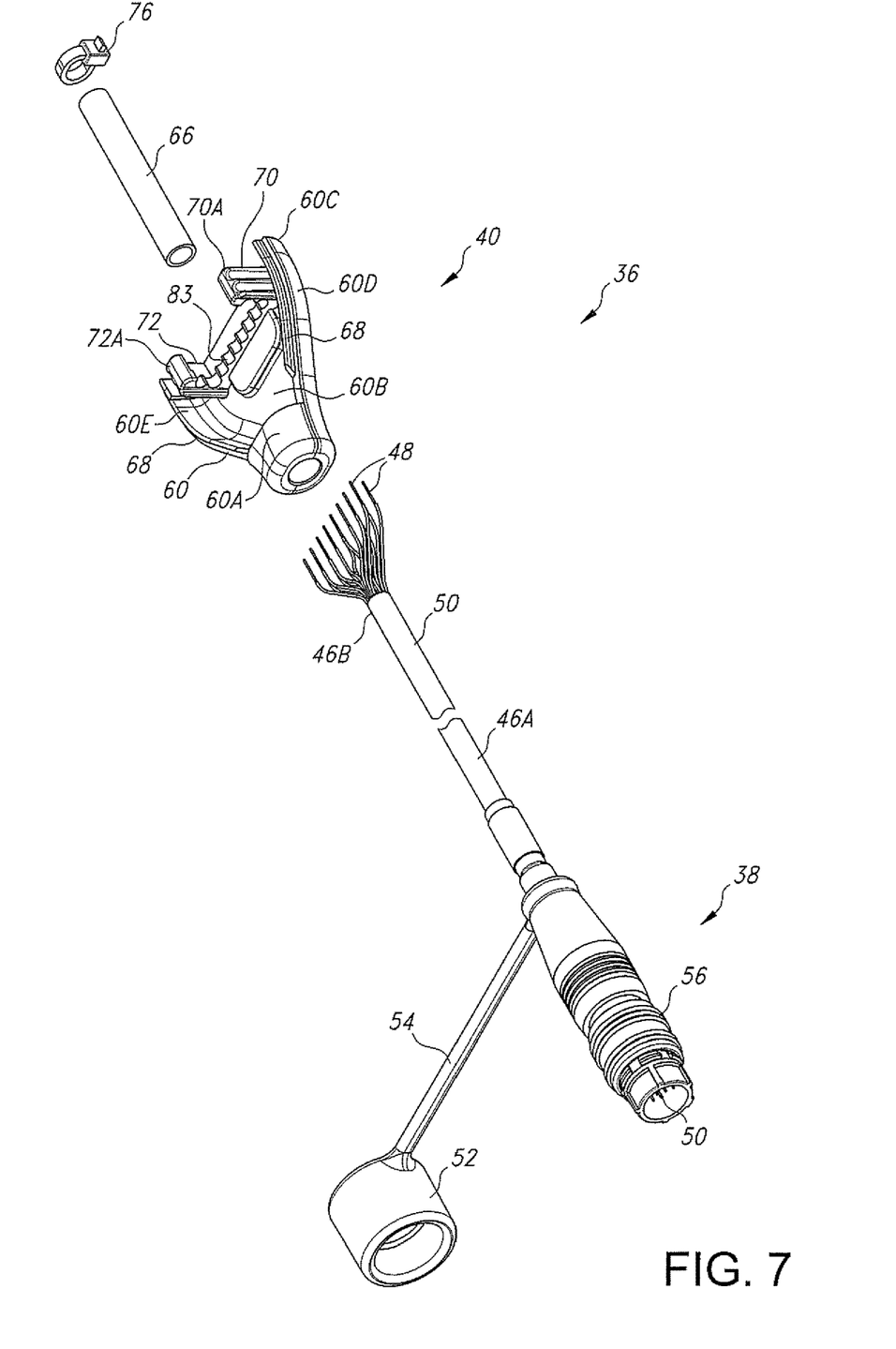
FIG. 7 is a perspective illustration of the cable assembly 36 with part of its distal connector 40 in an exploded view.
Figure 15:
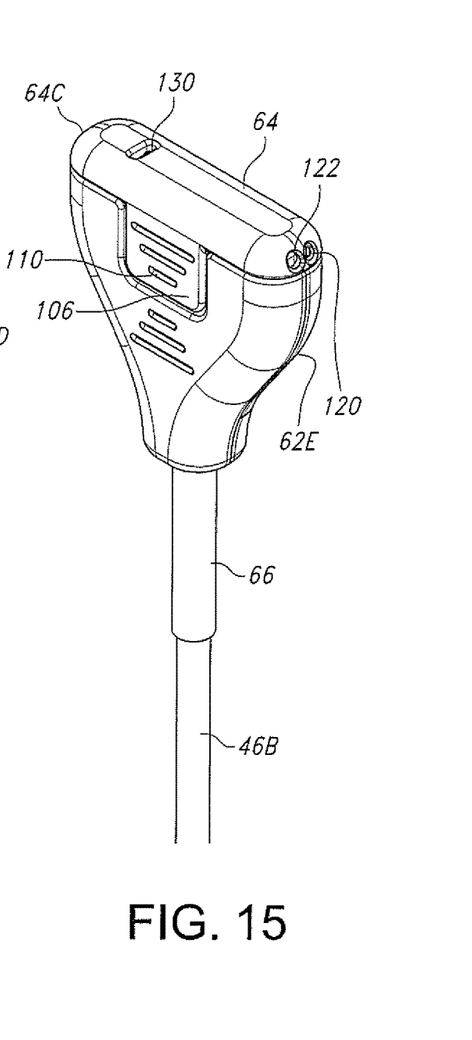
FIG. 15 is a perspective view of the distal connector 40 for the cable assembly 36 with the cover plate 62 connected to the base plate 60 and the header 64 is the closed position.

As shown in FIGS. 4 and 15, the header 64 is further provided with a pair of side-by-side openings 120, 122 extending inwardly into the curved end wall 64D. A registration tab 124 extends upwardly from the sidewall 60E of the base plate 60 and is received in a matching recess 126 (FIG. 8) in the header 64. Recess 126 resides adjacent to the side-by-side openings 120, 122 and serves as a stop to prevent the proximal end of the signal delivery lead 18 from being moved into one of the openings 120, 122 with the header 64 in a closed position seated on the distal open ends 60D and 62C of the respective base and cover plates 60, 62.

To use the cable assembly 36, the practitioner manipulates the header 64 by squeezing the opposed finger tabs 106, 108 and moving the header 64 away from the mated base and cover plates 60, 62. In its fully extended or open position, the registration tab 124 is no longer aligned with and received in the matching recess 126. This fully open position is apparent to the practitioner when opposed visual indicators 128 (FIGS. 8 and 13) are seen. For example, the distal housing comprising the mating base and cover plates 60 and 62 closed by the header 64 can be molded from any one of many suitable polymeric materials to have a white or off-white appearance. The visual indicators 128 are of a color that readily contrasts with white or off-white such as red, green, blue, and the like.

With the proximal connector 38 of the cable assembly 36 of the present invention connected to an external trial stimulator 34 and with the distal housing 58 of the distal connector 40 in its fully open position having the header 64 spaced above the open ends 60D, 62C of the base and cover plates 60 and 62, as apparent by seeing the visual indicators 128, the practitioner moves the distal end of at least one and possibly two signal delivery devices 18 into the side-by-side openings 120, 122 until the leads "bottom out" adjacent to the opposed curved end wall 64C of the header 64. An inspection window 130 (FIGS. 13 and 15) allows for visual observation that the signal delivery devices 18 are fully inserted into the side-by-side openings 120, 122 in the header 64 of the distal housing 58.

With the signal delivery devices 18 inserted into the header 64, the header is moved from the open position to the closed position (FIGS. 3, 4 and 15) seated on the distal open ends 60D, 62C of the base and cover plates 60 and 62. As previously described, the spring-loaded relationship of the distal contact pins 90 with the contact sleeves 88 of the sixteen electrical contact assemblies 74 enables each contact pin 90 to actuate axially back and forth along its contact sleeve 88 as the header 64 supporting the signal delivery devices 18 is moved from the open to the closed position and back to the open position. This enables electrical contacts at the distal ends of two signal delivery devices 18 to ride over the dome-shaped ends 90A of the distal contact pins 90 to help ensure that the contact pins are in electrical continuity with the signal delivery devices. The practitioner is now ready to test the efficacy of the therapy delivery device or devices 18 in an initial position.

Thus, with the header 64 in the open position, dome-shaped distal end 90A of the plurality of electrical contact assemblies 74 reside along a first imaginary plane spaced distally outwardly with respect to the distal open ends 60D, 62C of the base and cover plates 60 and 62, and wherein with the header 64 in the closed position, the distal ends 90A of the plurality of electrical contact assemblies 74 reside along a second imaginary plane that is spaced closer to the housing distal open end 60D, 62C than when the header 64 is in the open position and the plurality of electrical contact assemblies 74 reside along the first imaginary plane.

If needed, the practitioner can disconnect the cable assembly 36 from the therapy delivery device or devices 18, reposition the therapy delivery device or devices, reconnect the cable assembly 36 and reapply electrical stimulation from the external trial stimulator 34. This process is performed iteratively until the practitioner obtains the desired position for the signal delivery device or devices 18.

As previously described, in a representative protocol the patient 12 receives therapy for a limited trial period, for example a one-week trial period, during which time the patient wears the cable assembly 36 and the external trial stimulator 34 outside the body. Assuming the trial therapy is effective or shows the promise of being effective, the practitioner then replaces the external trial stimulator 34 and the cable assembly 36 with the implanted pulse generator 16 connected to the therapy delivery device or devices 18 or connected to the lead extension 22 in turn connected to the therapy delivery device or devices, and programs the pulse generator 16 with parameters selected based on the experience gained during the trial period. Optionally, the practitioner can also replace the therapy delivery device or devices 18.

It is appreciated that various modifications to the inventive concepts described herein may be apparent to those of ordinary skill in the art without departing from the spirit and scope of the present invention as defined by the appended claims.

What is claimed is:

1. A cable assembly for a patient treatment system, the cable assembly comprising:

a) an electrical cable comprising a plurality of cable electrical conductors extending from a cable proximal end to a cable distal portion having a cable distal end;
 b) a proximal connector connected to the proximal end of the cable, the proximal connector having a plurality of cable proximal connector contacts electrically connected to a respective one of the plurality of cable electrical conductors, wherein the proximal connector is configured to be releasably electrically connected to an electrical stimulation device; and
 c) a distal connector connected to the distal end of the cable, the distal connector comprising:
  i) a housing extending from a housing proximal end secured to the cable distal portion to a housing distal portion having a housing distal open end;
  ii) a plurality of electrical contact assemblies residing in the housing, the plurality of electrical contact assemblies being electrically connected to a respective one of the plurality of cable electrical conductors; and
  iii) a header movably secured to the housing distal portion to selectively open and close the housing distal open end as the header is manipulated from a closed position to an open position and is further manipulated from the open position to the closed position, wherein the header has at least one longitudinally extending opening that is configured to slidably receive the proximal end of a therapy delivery device,
 d) wherein with a proximal end of a lead received in the at least one longitudinally extending opening in the header, an electrical contact of the therapy delivery device is in electrical continuity with a respective one of the plurality of electrical contact assemblies.

2. The cable assembly of claim 1, wherein, with the header in the open position, distal ends of the plurality of electrical contact assemblies reside along a first imaginary plane spaced distally outwardly with respect to the housing distal open end, and wherein with the header in the closed position, the distal ends of the plurality of electrical contact assemblies reside along a second imaginary plane that is spaced closer to the housing distal open end than when the header is in the open position and the plurality of electrical contact assemblies reside along the first imaginary plane.

3. The cable assembly of claim 1, wherein a manifold is disposed inside the housing, the manifold comprising a plurality of via holes that receive a respective one of the plurality of electrical contact assemblies.

4. The cable assembly of claim 1, wherein the header has two side-by-side longitudinally extending openings that are each configured to slidably receive the proximal end of a therapy delivery device.

5. The cable assembly of claim 4, wherein the plurality of via holes in a manifold are arranged in two side-by-side rows that align with a respective one of the two side-by-side longitudinally extending openings in the header.

6. The cable assembly of claim 1, wherein the housing of the distal connector is provided with at least one visual indicator that is exposed when the header is in the open position.

7. The cable assembly of claim 6, wherein there are two visual indicators, one of them located on opposed sides of the distal connector.

8. The cable assembly of claim 1, wherein the header comprises an inspection window that visually indicates when the proximal end of a therapy delivery device resides in the at least one longitudinally extending opening in the header.

9. The cable assembly of claim 1, wherein a strain-relief sleeve is fitted onto the cable distal portion.

10. The cable assembly of claim 1, wherein a pair of opposed finger tabs depending from the header are configured to aid in manipulation of the header between the open and closed positions.

11. The cable assembly of claim 10, wherein the opposed finger tabs support at least one inwardly facing vertical ridge that mates with an outwardly facing vertical groove in the housing.

12. The cable assembly of claim 1, wherein the housing is comprised of a base plate mated to a cover plate to thereby define the housing distal open end.

13. The cable assembly of claim 1, wherein a manifold disposed inside the housing comprises a plurality of via holes that support a respective one of the plurality of electrical contact assemblies, and wherein the housing comprises a first pair of inwardly facing L-shaped hooks that contain the manifold, the first pair of inwardly facing L-shaped hooks of the housing comprising at least two horizontal grooves on an outer surface thereof, wherein the at least two horizontal grooves of the first pair of inwardly facing L-shaped hooks are in a snap-fit engagement with a second pair of inwardly facing L-shaped hooks of the header to thereby define the closed position for the distal connector with the second pair of L-shaped hooks of the header in a snap-fit engagement with a proximal most one of the at least two horizontal grooves and to define the open position for the distal connector with the second pair of L-shaped hooks of the header in a snap-fit engagement with a distal most one of the at least two horizontal grooves.

14. The cable assembly of claim 1, wherein, with the header in the closed position, a registration tab extending upwardly from the housing adjacent to the housing distal open end thereof is received in a matching recess in the header, and wherein, with the header in the open position, the registration tab resides outside the matching recess.

15. The cable assembly of claim 1, wherein the proximal connector is configured to be releasably electrically connected directly to an electrical stimulation device.

16. The cable assembly of claim 1, wherein the proximal connector comprises a removable protective cap.

17. A cable assembly for a patient treatment system, the cable assembly comprising:
   a) an electrical cable comprising a plurality of cable electrical conductors extending from a cable proximal end to a cable distal portion having a cable distal end;
   b) a proximal connector connected to the proximal end of the cable, the proximal connector having a plurality of cable proximal connector contacts electrically connected to a respective one of the plurality of cable electrical conductors, wherein the proximal connector is configured to be releasably electrically connected to an electrical stimulation device; and
   c) a distal connector connected to the distal end of the cable, the distal connector comprising:
      i) a housing extending from a housing proximal end secured to the cable distal portion to a housing distal portion having a housing distal open end;
      ii) a plurality of electrical contact assemblies residing in the housing, the plurality of electrical contact assemblies being electrically connected to a respective one of the plurality of cable electrical conductors;
      iii) a manifold disposed inside the housing, the manifold comprising a plurality of via holes that receive a respective one of the plurality of electrical contact assemblies, wherein the housing comprises a first pair of inwardly facing L-shaped hooks that contain the manifold; and
      iv) a header movably secured to the housing distal portion, the header having at least one longitudinally extending opening that is configured to slidably receive the proximal end of a therapy delivery device, wherein the header comprises a second pair of inwardly facing L-shaped hooks that depend from a header inner surface,
      v) wherein the first pair of inwardly facing L-shaped hooks of the housing comprise at least two horizontal grooves on an outer surface thereof that are in a snap-fit engagement with the second pair of inwardly facing L-shaped hooks of the header to thereby define a closed position for the distal connector with the second pair of L-shaped hooks of the header in a snap-fit engagement with a proximal most one of the at least two horizontal grooves and to define an open position for the distal connector with the second pair of L-shaped hooks of the header in a snap-fit engagement with a distal most one of the at least two horizontal grooves, and
   d) wherein with the proximal end of a lead received in the at least one longitudinally extending opening in the header and with the header in the closed position, an electrical contact of the therapy delivery device is in electrical continuity with a respective one of the plurality of electrical contact assemblies.

18. The cable assembly of claim 17, wherein the header has two side-by-side longitudinally extending openings that are each configured to slidably receive the proximal end of a therapy delivery device.

19. The cable assembly of claim 18, wherein the plurality of via holes in the manifold are arranged in two side-by-side rows that align with a respective one of the two side-by-side longitudinally extending openings in the header.

20. The cable assembly of claim 17, wherein the housing of the distal connector is provided with at least one visual indicator that is exposed when the header is in the open position.

21. The cable assembly of claim 17, wherein the header comprises an inspection window that visually indicates when the proximal end of a therapy delivery device resides in the at least one longitudinally extending opening in the header.

22. The cable assembly of claim 17, wherein a pair of opposed finger tabs depending from the header are configured to aid in manipulation of the header between the open and closed positions, and wherein the opposed finger tabs support at least one inwardly facing vertical ridge that mates with an outwardly facing vertical groove in the housing.

23. The cable assembly of claim 17, wherein a registration tab extending upwardly from the housing adjacent to the housing distal open end thereof is received in a matching recess in the header with the header in the closed position, and wherein with the header in the open position, the registration tab resides outside the matching recess.

* * * * *